(12) United States Patent
Morita

(10) Patent No.: US 11,540,797 B2
(45) Date of Patent: Jan. 3, 2023

(54) TOMOGRAPHIC IMAGE GENERATION APPARATUS, METHOD, AND PROGRAM

(71) Applicant: FUJIFILM CORPORATION, Tokyo (JP)

(72) Inventor: Junya Morita, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 620 days.

(21) Appl. No.: 16/558,331

(22) Filed: Sep. 3, 2019

(65) Prior Publication Data

US 2020/0100752 A1 Apr. 2, 2020

(30) Foreign Application Priority Data

Sep. 27, 2018 (JP) .............................. JP2018-182725

(51) Int. Cl.
*A61B 6/02* (2006.01)
*G06T 11/00* (2006.01)
*A61B 6/00* (2006.01)

(52) U.S. Cl.
CPC ............ *A61B 6/5205* (2013.01); *A61B 6/025* (2013.01); *A61B 6/502* (2013.01); *A61B 6/5264* (2013.01); *G06T 11/008* (2013.01)

(58) Field of Classification Search
CPC ....... A61B 6/025; A61B 6/5264; A61B 6/527; A61B 6/5276
See application file for complete search history.

(56) References Cited

U.S. PATENT DOCUMENTS 9,858,663 B2  1/2018  Penney et al.
10,993,689 B2 * 5/2021 Palma .................... G06T 7/0016
(Continued)

FOREIGN PATENT DOCUMENTS

| JP | 2013-261 A | 1/2013 |
| JP | 2014-128716 A | 7/2014 |
| JP | 2016-064119 A | 4/2016 |

OTHER PUBLICATIONS

English language translation of the following: Office action dated Aug. 3, 2021 from the JPO in a Japanese patent application No. 2018-182725 corresponding to the instant patent application. This office action translation is submitted now in order to supplement the understanding of the cited reference which is being disclosed in the instant Information Disclosure Statement.

(Continued)

*Primary Examiner* — Colin T. Sakamoto
(74) *Attorney, Agent, or Firm* — Solaris Intellectual Property Group, PLLC

(57) ABSTRACT

An image acquisition unit acquires a plurality of projection images corresponding to a plurality of radiation source positions at the time of tomosynthesis imaging, the plurality of projection images being generated by causing an imaging apparatus to perform tomosynthesis imaging. A positional shift amount derivation unit derives a positional shift amount between the plurality of projection images based on body movement of the subject with a reference projection image generated at a radiation source position where an optical axis of the radiation emitted from the radiation source is perpendicular to a detection surface of the detection unit, among the plurality of projection images, as a reference. A reconstruction unit generates a tomographic image of at least one tomographic plane of the subject by reconstructing the plurality of projection images while correcting the positional shift amount.

10 Claims, 12 Drawing Sheets

(56) References Cited

U.S. PATENT DOCUMENTS

| | | | | |
|---|---|---|---|---|
| 2008/0123812 A1* | 5/2008 | Sabol | ............ | A61B 6/527 |
| | | | | 600/407 |
| 2009/0262887 A1* | 10/2009 | Iordache | ............ | A61B 6/583 |
| | | | | 378/37 |
| 2010/0119116 A1* | 5/2010 | Nishimura | ............ | A61B 6/025 |
| | | | | 382/107 |
| 2010/0171822 A1* | 7/2010 | Sawada | ............ | G06T 11/006 |
| | | | | 378/27 |
| 2012/0033868 A1* | 2/2012 | Ren | ............ | A61B 6/025 |
| | | | | 378/21 |
| 2015/0243025 A1* | 8/2015 | Berlinger | ............ | A61B 6/0492 |
| | | | | 382/128 |
| 2017/0281110 A1* | 10/2017 | Mandelkern | ............ | A61B 6/469 |
| 2019/0059841 A1* | 2/2019 | Palma | ............ | G06T 7/246 |
| 2020/0178926 A1* | 6/2020 | Kshirsagar | ............ | A61B 6/465 |
| 2020/0196971 A1* | 6/2020 | Laviola | ............ | A61B 6/0414 |
| 2020/0222023 A1* | 7/2020 | Wong | ............ | A61B 6/465 |
| 2021/0204899 A1* | 7/2021 | Palma | ............ | A61B 8/481 |

OTHER PUBLICATIONS

Wataru Fukuda et al., "Improved Tomosynthesis Reconstruction using Super-resolution and Iterative Techniques", Fujifilm Research & Development, Dec. 7, 2015, pp. 1-7, XP055645591.
Extended European Search Report dated Dec. 2, 2019, issued in corresponding EP Patent Application No. 19195442.9.

* cited by examiner

TOMOGRAPHIC IMAGE GENERATION APPARATUS, METHOD, AND PROGRAM

CROSS REFERENCE TO RELATED APPLICATIONS

The present application claims priority under 35 U.S.C. § 119 to Japanese Patent Application No. 2018-182725 filed on Sep. 27, 2018. The above application is hereby expressly incorporated by reference, in its entirety, into the present application.

BACKGROUND

Technical Field

The present disclosure relates to a tomographic image generation apparatus, a tomographic image generation method, and a tomographic image generation program for acquiring a plurality of projection images by imaging a subject at each of a plurality of radiation source positions and generating a tomographic image from the plurality of projection images.

Related Art

In recent years, in radiation image capturing apparatuses using radiation such as X-rays and gamma rays, in order to observe an affected part in more detail, tomosynthesis imaging has been proposed in which imaging is performed by moving a radiation source to emit radiation to a subject from a plurality of radiation source positions and a plurality of projection images acquired by the imaging are added up to generate a tomographic image in which a desired tomographic plane is emphasized. In the tomosynthesis imaging, a plurality of projection images are acquired by imaging the subject at a plurality of radiation source positions by moving the radiation source in parallel to a radiation detector or moving the radiation source so as to draw a circular or elliptical arc according to the characteristics of the imaging apparatus and required tomographic images, and the projection images are reconstructed using, for example, a back projection method, such as a simple back projection method or a filtered back projection method, to generate a tomographic image.

By generating such a tomographic image on a plurality of tomographic planes of the subject, it is possible to separate structures overlapping each other in a depth direction in which the tomographic planes are aligned. Therefore, it is possible to find a lesion that has been difficult to detect in a two-dimensional image acquired by simple imaging in the related art. The simple imaging is an imaging method for acquiring one two-dimensional image, which is a transmission image of a subject, by emitting radiation to the subject once.

On the other hand, the tomosynthesis imaging has a problem that a reconstructed tomographic image is blurred due to the mechanical error of the imaging apparatus and the influence of body movement of the subject due to the time difference of imaging at the plurality of radiation source positions. In a case where the tomographic image is blurred as described above, it is difficult to find a lesion such as minute calcification, which is useful for early detection of breast cancer, particularly in a case where the breast is a subject.

For this reason, a method of correcting body movement in the case of generating a tomographic image from a projection image acquired by tomosynthesis imaging has been proposed. For example, JP2016-064119A has proposed a method in which a plurality of tomographic plane projection images are acquired by projecting the pixel values of a plurality of projection images acquired by tomosynthesis imaging onto coordinate positions on a desired tomographic plane of a subject based on the positional relationship between the radiation source position and a radiation detector at the time of imaging for each of the plurality of projection images while maintaining the pixel values of the plurality of projection images, positional shift between the plurality of tomographic plane projection images is corrected, and a tomographic image is generated from the plurality of tomographic plane projection images subjected to positional shift correction.

On the other hand, a method has been proposed in which a two-dimensional image (hereinafter, referred to as a composite two-dimensional image) corresponding to a radiation image acquired by simple imaging is generated by projecting a tomographic image acquired by tomosynthesis imaging in the depth direction of a subject in which tomographic planes are aligned. For example, JP2014-128716A has proposed a method of acquiring a composite two-dimensional image from a tomographic image and a projection image.

In the case of correcting body movement as described in JP2016-064119A, it is important to determine which projection image is to be used as a reference in determining the image quality of the tomographic image to be generated. However, JP2016-064119A and JP2014-128716A do not describe which image is to be used as a reference. The tomographic image and the composite two-dimensional image are often used for diagnosis together with two-dimensional images acquired by simple imaging. For this reason, it is diagnostically important to take correspondence between the positions of the tomographic image and the composite two-dimensional image and the position of the two-dimensional image acquired by simple imaging.

SUMMARY OF THE INVENTION

The invention has been made in view of the aforementioned circumstances, and the object of the invention is to make it possible to acquire a high-quality tomographic image in which the influence of body movement is appropriately reduced.

A tomographic image generation apparatus according to the invention comprises: an image acquisition unit that acquires a plurality of projection images corresponding to a plurality of radiation source positions, the plurality of projection images being generated by causing an imaging apparatus to perform tomosynthesis imaging in which a radiation source is moved relative to a detection unit in order to emit radiation to a subject at the plurality of radiation source positions according to movement of the radiation source; a positional shift amount derivation unit that derives a positional shift amount between the plurality of projection images based on body movement of the subject with a reference projection image generated at a radiation source position where an optical axis of the radiation emitted from the radiation source is perpendicular to a detection surface of the detection unit, among the plurality of projection images, as a reference; and a reconstruction unit that generates a tomographic image of at least one tomographic plane of the subject by reconstructing the plurality of projection images while correcting the positional shift amount.

"The radiation source is moved relative to the detection unit" includes a case of moving only the radiation source, a case of moving only the detection unit, and a case of moving both the radiation source and the detection unit.

"The optical axis of the radiation is perpendicular to the detection surface of the detection unit" means that the optical axis of the radiation crosses the detection surface of the detection unit at an angle of 90°. However, without being limited to this, a case where the optical axis of the radiation crosses the detection surface of the detection unit with a certain degree of error with respect to 90° may be included. For example, a case where the optical axis of the radiation crosses the detection surface of the detection unit with an error of about ±3° with respect to 90° is included in "the optical axis of the radiation is perpendicular to the detection surface of the detection unit" in the invention.

In the tomographic image generation apparatus according to the invention, the reconstruction unit may reconstruct the plurality of projection images to generate a plurality of temporary tomographic images. The positional shift amount derivation unit may detect a plurality of different feature points in the plurality of temporary tomographic images, derive a temporary positional shift amount between the plurality of projection images with the reference projection image as a reference for the plurality of different feature points, interpolate temporary positional shift amounts derived for the plurality of different feature points, and derive a positional shift amount of each pixel position in each of the plurality of projection images with respect to each of coordinate positions of the plurality of temporary tomographic images.

In the tomographic image generation apparatus according to the invention, the positional shift amount derivation unit may detect at least one corresponding point in the plurality of projection images, project the corresponding points in the plurality of projection images onto at least one tomographic plane of the subject based on a positional relationship between the detection unit and the radiation source position at the time of imaging for each of the plurality of projection images, and derive the positional shift amount based on a positional relationship between the projected corresponding points.

The tomographic image generation apparatus according to the invention may further comprise a combining unit that generates a composite two-dimensional image by combining two or more tomographic images among the plurality of tomographic images or at least one of the plurality of tomographic images and the reference projection image.

In the tomographic image generation apparatus according to the invention, the subject may be a breast.

A tomographic image generation method according to the invention comprises: acquiring a plurality of projection images corresponding to a plurality of radiation source positions, the plurality of projection images being generated by causing an imaging apparatus to perform tomosynthesis imaging in which a radiation source is moved relative to a detection unit in order to emit radiation to a subject at the plurality of radiation source positions according to movement of the radiation source; deriving a positional shift amount between the plurality of projection images based on body movement of the subject with a reference projection image generated at a radiation source position where an optical axis of the radiation emitted from the radiation source is perpendicular to a detection surface of the detection unit, among the plurality of projection images, as a reference; and generating a tomographic image of at least one tomographic plane of the subject by reconstructing the plurality of projection images while correcting the positional shift amount.

A tomographic image generation program according to the invention causes a computer to execute: a step of acquiring a plurality of projection images corresponding to a plurality of radiation source positions, the plurality of projection images being generated by causing an imaging apparatus to perform tomosynthesis imaging in which a radiation source is moved relative to a detection unit in order to emit radiation to a subject at the plurality of radiation source positions according to movement of the radiation source; a step of deriving a positional shift amount between the plurality of projection images based on body movement of the subject with a reference projection image generated at a radiation source position where an optical axis of the radiation emitted from the radiation source is perpendicular to a detection surface of the detection unit, among the plurality of projection images, as a reference; and a step of generating a tomographic image of at least one tomographic plane of the subject by reconstructing the plurality of projection images while correcting the positional shift amount.

Another tomographic image generation apparatus according to the invention comprises: a memory that stores commands to be executed by a computer; and a processor configured to execute the stored commands. The processor executes: a step of acquiring a plurality of projection images corresponding to a plurality of radiation source positions, the plurality of projection images being generated by causing an imaging apparatus to perform tomosynthesis imaging in which a radiation source is moved relative to a detection unit in order to emit radiation to a subject at the plurality of radiation source positions according to movement of the radiation source; a step of deriving a positional shift amount between the plurality of projection images based on body movement of the subject with a reference projection image generated at a radiation source position where an optical axis of the radiation emitted from the radiation source is perpendicular to a detection surface of the detection unit, among the plurality of projection images, as a reference; and a step of generating a tomographic image of at least one tomographic plane of the subject by reconstructing the plurality of projection images while correcting the positional shift amount.

According to the invention, it is possible to acquire a high-quality tomographic image in which the influence of body movement is appropriately reduced. In addition, the correspondence between the position of the composite two-dimensional image or the tomographic image subjected to body movement correction and the position of the two-dimensional image acquired by simple imaging can be easily taken.

DETAILED DESCRIPTION

Figure 1:
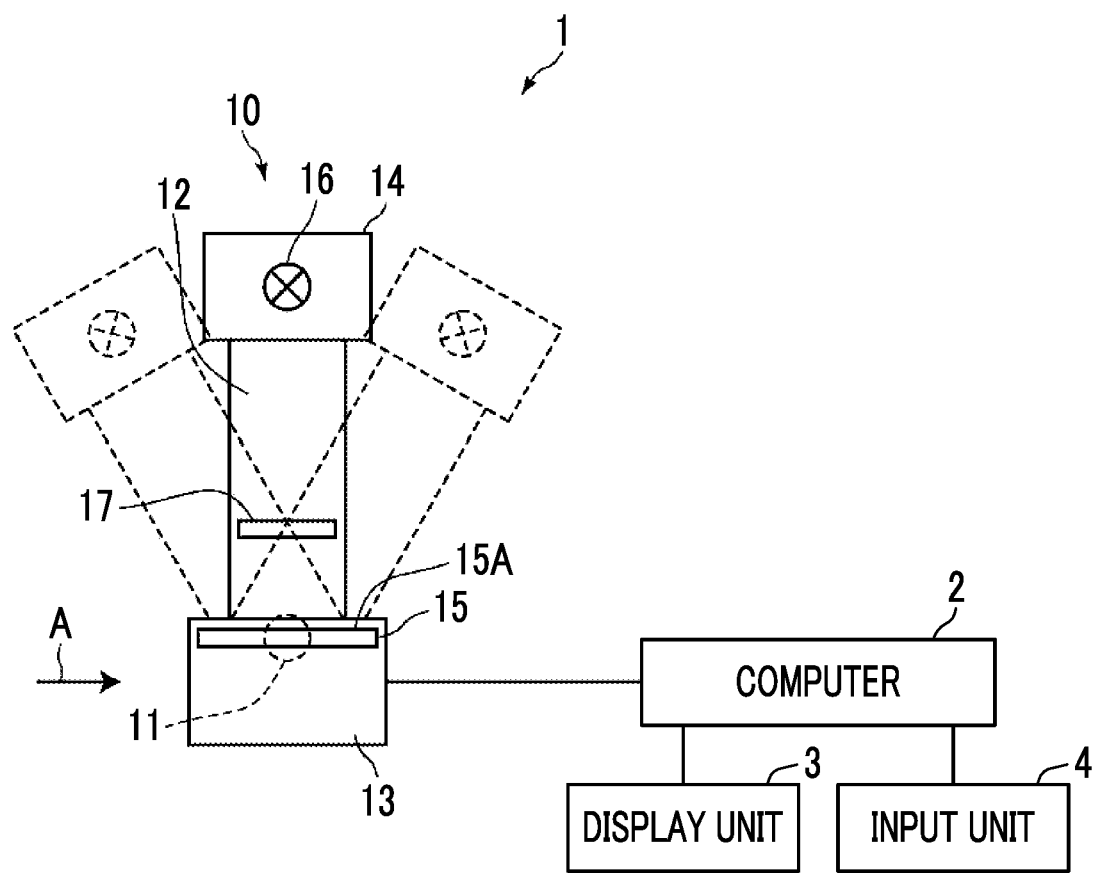
FIG. 1 is a schematic configuration diagram of a radiation image capturing apparatus to which a tomographic image generation apparatus according to a first embodiment of the invention is applied.
Figure 2:
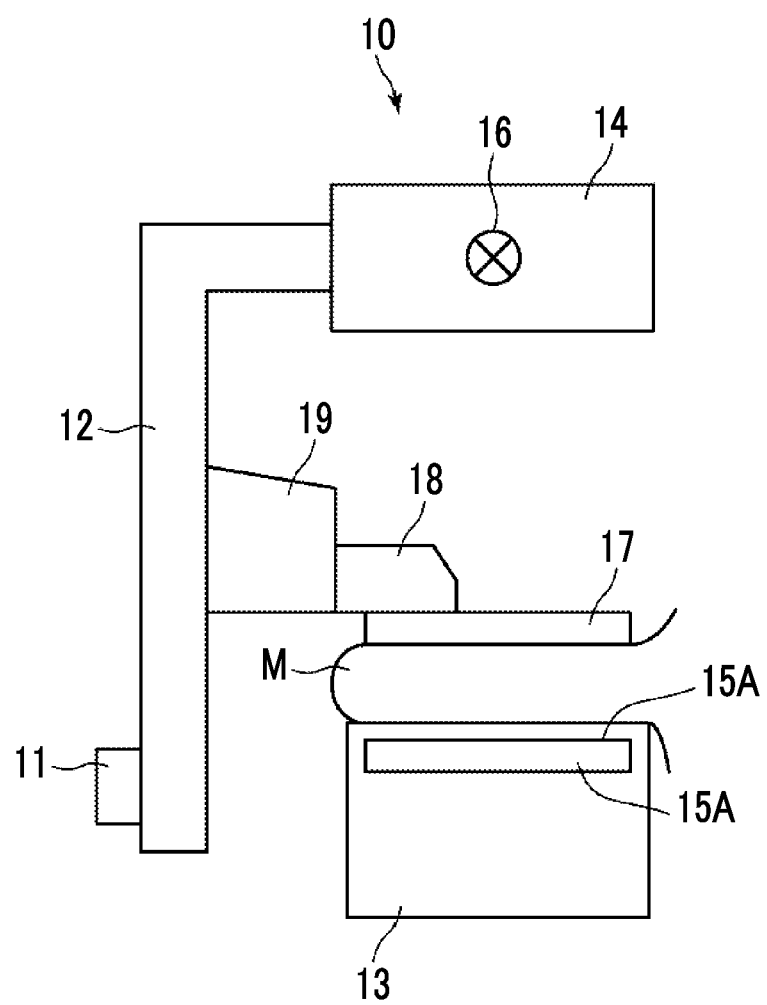
FIG. 2 is a diagram of the radiation image capturing apparatus as viewed from the direction of arrow A in FIG. 1.

Hereinafter, embodiments of the invention will be described with reference to the diagrams. FIG. 1 is a schematic configuration diagram of a radiation image capturing apparatus to which a tomographic image generation apparatus according to a first embodiment of the invention is applied, and FIG. 2 is a diagram of the radiation image capturing apparatus as viewed from the direction of arrow A in FIG. 1. A radiation image capturing apparatus 1 is a mammography imaging apparatus that acquires a plurality of radiation images, that is, a plurality of projection images, by imaging a breast M, which is a subject, from a plurality of radiation source positions in order to generate a tomographic image by performing tomosynthesis imaging of the breast. As shown in FIG. 1, the radiation image capturing apparatus 1 comprises an imaging unit 10, a computer 2 connected to the imaging unit 10, and a display unit 3 and an input unit 4 connected to the computer 2.

The imaging unit 10 comprises an arm unit 12 connected to a base (not shown) by a rotary shaft 11. An imaging table 13 is attached to one end portion of the arm unit 12, and a radiation emission unit 14 is attached to the other end portion so as to face the imaging table 13. The arm unit 12 is configured so that only the end portion to which the radiation emission unit 14 is attached can rotate. Therefore, it is possible to rotate only the radiation emission unit 14 with the imaging table 13 fixed. The rotation of the arm unit 12 is controlled by the computer 2.

A radiation detector 15, such as a flat panel detector, is provided in the imaging table 13. The radiation detector 15 has a detection surface 15A of radiation, such as X-rays. In addition, a circuit board on which a charge amplifier for converting a charge signal read from the radiation detector 15 into a voltage signal, a correlated double sampling circuit for sampling the voltage signal output from the charge amplifier, an analog digital (AD) conversion unit for converting the voltage signal into a digital signal, and the like are provided is provided inside the imaging table 13. The radiation detector 15 corresponds to a detection unit. Although the radiation detector 15 is used as a detection unit in the present embodiment, the detection unit is not limited to the radiation detector 15 as long as radiation can be detected and converted into an image.

The radiation detector 15 can perform recording and reading of a radiation image repeatedly. A so-called direct-type radiation detector that converts radiation, such as X-rays, directly into electric charges may be used, or a so-called indirect-type radiation detector that converts radiation into visible light and then converts the visible light into a charge signal may be used. As a method of reading a radiation image signal, it is desirable to use a so-called TFT reading method in which a radiation image signal is read by ON and OFF of a thin film transistor (TFT) switch or a so-called optical reading method in which a radiation image signal is read by emission of reading light. However, other methods may also be used without being limited to the above methods.

An X-ray source 16, which is a radiation source, is housed inside the radiation emission unit 14. The timing of emission of X-rays, which are radiation from the X-ray source 16, and X-ray generation conditions in the X-ray source 16, that is, selection of target and filter materials, a tube voltage, an emission time, and the like are controlled by the computer 2.

A compression plate 17 disposed above the imaging table 13 in order to compress the breast M, a support unit 18 for supporting the compression plate 17, and a moving mechanism 19 for moving the support unit 18 in the vertical direction in FIGS. 1 and 2 are provided in the arm unit 12. Information of the distance between the compression plate 17 and the imaging table 13, that is, the compression thickness, is input to the computer 2.

The display unit 3 is a display device, such as a cathode ray tube (CRT) or a liquid crystal monitor, and displays a projection image and a tomographic image acquired as will be described later, a message required for the operation, and the like. The display unit 3 may include a speaker for outputting sound.

The input unit 4 includes an input device, such as a keyboard, a mouse, or a touch panel, and receives an operation of the radiation image capturing apparatus 1 by the operator. In addition, the input unit 4 receives an input of various kinds of information, such as imaging conditions, and an instruction to modify information, which are required to perform tomosynthesis imaging. In the present embodiment, each unit of the radiation image capturing apparatus 1 operates according to the information input from the input unit 4 by the operator.

A tomographic image generation program according to the present embodiment is installed on the computer 2. In the present embodiment, the computer may be a workstation or a personal computer that is directly operated by the operator, or may be a server computer connected to these through a network. The tomographic image generation program is distributed in a state in which the tomographic image generation program is recorded on a recording medium, such as a digital versatile disc (DVD) or a compact disc read only memory (CD-ROM), and is installed onto the computer from the recording medium. Alternatively, the tomographic image generation program is stored in a storage device of a server computer connected to the network or in a network storage (hereinafter, referred to as an external storage device) so as to be accessible from the outside, and is downloaded and installed on the computer as necessary.

Figure 3:
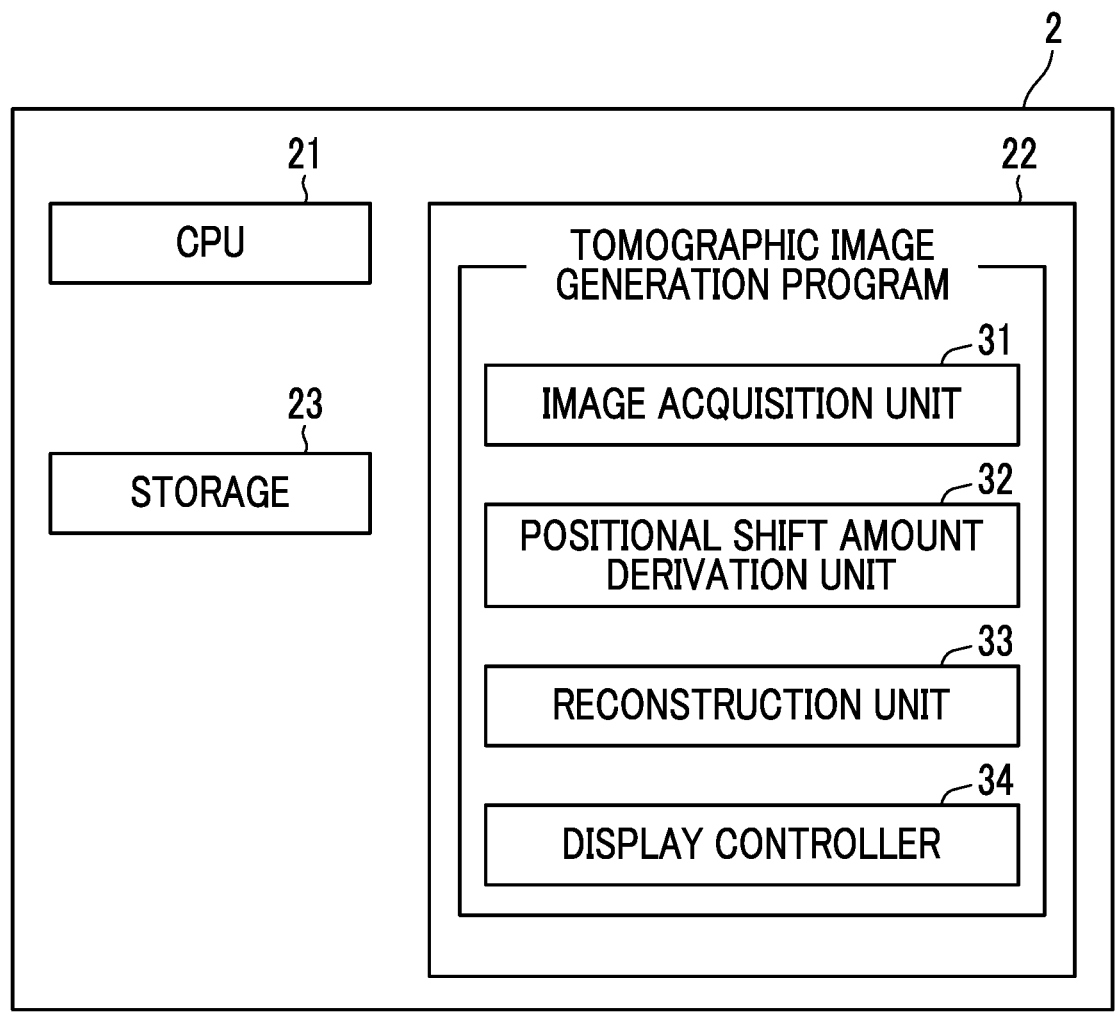
FIG. 3 is a diagram showing the schematic configuration of an imaging control device realized by installing a tomographic image generation program on a computer in the first embodiment.

FIG. 3 is a diagram showing the schematic configuration of a tomographic image generation apparatus realized by installing a tomographic image generation program according to a first embodiment on the computer 2. As shown in FIG. 3, the tomographic image generation apparatus comprises a central processing unit (CPU) 21, a memory 22, and a storage 23 as the configuration of a standard computer.

The storage 23 is a storage device, such as a hard disk drive or a solid state drive (SSD), and stores various kinds of information including a program for driving each unit of the radiation image capturing apparatus 1 and the tomographic image generation program. In addition, a projection image acquired by tomosynthesis imaging and a tomographic image and a temporary tomographic image generated as will be described later are stored in the storage 23.

The memory 22 temporarily stores programs and the like stored in the storage 23 so that the CPU 21 executes various kinds of processing. As processing to be executed by the CPU 21, the tomographic image generation program defines: image acquisition processing for acquiring a plurality of projection images of the breast M corresponding to a plurality of radiation source positions by making the radiation image capturing apparatus 1 perform tomosynthesis imaging; positional shift amount derivation processing for deriving a positional shift amount between a plurality of projection images based on the body movement of the breast M with a reference projection image generated at a radiation source position where the optical axis of the X-ray emitted from the X-ray source 16 is perpendicular to the detection surface 15A of the radiation detector 15, among the plurality of projection images, as a reference; reconstruction processing for generating a tomographic image of at least one tomographic plane of the subject by reconstructing a plurality of projection images while correcting the positional shift amount; and display control processing for displaying a tomographic image and the like on the display unit 3.

Then, the CPU 21 executes these processes according to the tomographic image generation program, so that the computer 2 functions as an image acquisition unit 31, a positional shift amount derivation unit 32, a reconstruction unit 33, and a display controller 34.

In the case of performing image acquisition processing, the X-ray source 16 is moved by rotating the arm unit 12 around the rotary shaft 11, X-rays are emitted to the breast M as a subject at a plurality of radiation source positions according to the movement of the X-ray source 16 under the predetermined imaging conditions for tomosynthesis imaging, X-rays transmitted through the breast M are detected by the radiation detector 15, and a plurality of projection images Gi (i=1 to n, where n is the number of radiation source positions; for example, n=15) at a plurality of radiation source positions are acquired by the image acquisition unit 31.

Figure 4:
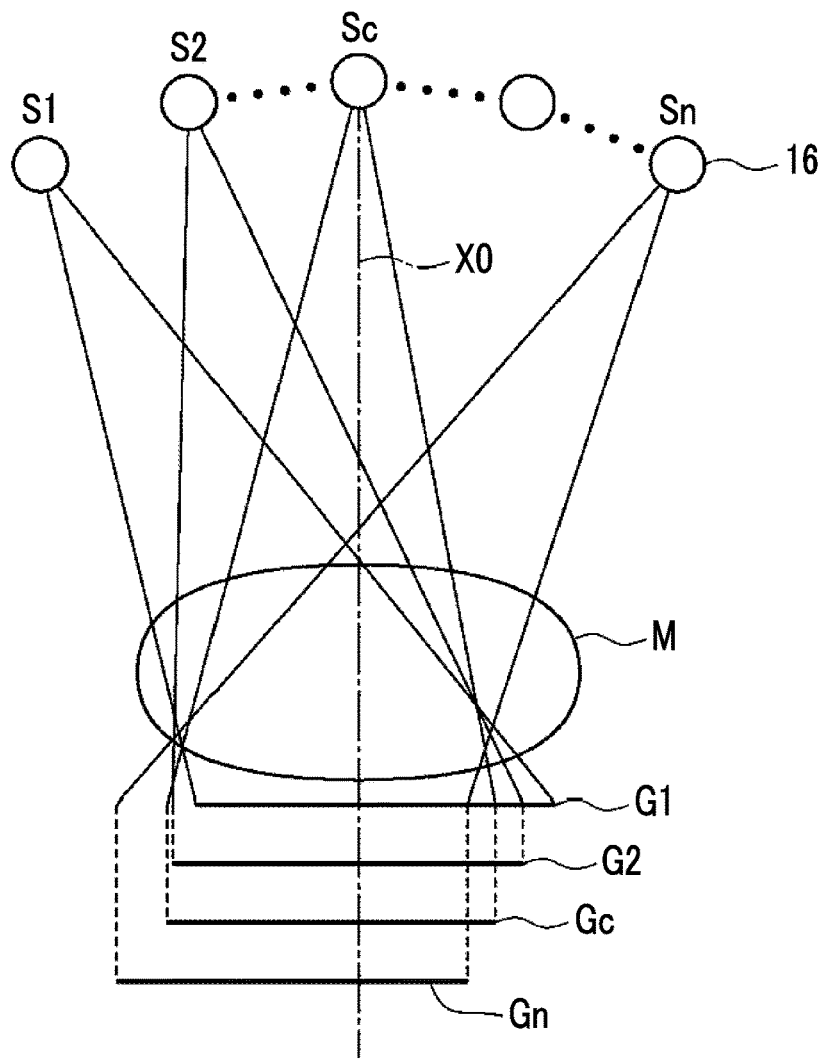
FIG. 4 is a diagram illustrating the acquisition of a projection image.

FIG. 4 is a diagram illustrating the acquisition of the projection image Gi. As shown in FIG. 4, the X-ray source 16 is moved to each radiation source position of S1, S2, . . . , Sn, the X-ray source 16 is driven at each radiation source position to irradiate the breast M with X-rays, and the X-rays transmitted through the breast M are detected by the radiation detector 15. As a result, projection images G1, G2, . . . , Gn are acquired corresponding to the radiation source positions S1 to Sn. At each of the radiation source positions S1 to Sn, X-rays of the same dose are emitted to the breast M. The plurality of acquired projection images Gi are stored in the storage 23. The plurality of projection images Gi may be acquired by a program separate from the tomographic image generation program and stored in the storage 23 or the external storage device. In this case, image acquisition unit 31 reads the plurality of projection images Gi stored in the storage 23 or the external storage device from the storage 23 or the external storage device for reconstruction processing and the like.

In FIG. 4, a radiation source position Sc is a radiation source position where an optical axis X0 of the X-ray emitted from the X-ray source 16 is perpendicular to the detection surface 15A of the radiation detector 15. The radiation source position Sc is referred to as a reference radiation source position Sc, and a projection image Gc acquired by irradiating the breast M with X-rays at the reference radiation source position Sc is referred to as a reference projection image Gc. Here, "the optical axis X0 of the X-ray emitted from the X-ray source 16 is perpendicular to the detection surface 15A of the radiation detector 15" means that the optical axis X0 of the X-ray crosses the detection surface 15A of the radiation detector 15 at an angle of 90°. However, without being limited to this, a case where the optical axis X0 of the X-ray crosses the detection surface 15A of the radiation detector 15 with a certain degree of error with respect to 90° may be included. For example, a case where the optical axis of the X-ray crosses the detection surface 15A of the radiation detector 15 with an error of about ±3° with respect to 90° is included in "the optical axis X0 of the X-ray is perpendicular to the detection surface 15A of the radiation detector 15" in the present embodiment.

The positional shift amount derivation unit 32 derives a positional shift amount between the plurality of projection images Gi based on the body movement of the breast M under tomosynthesis imaging with the reference projection image Gc as a reference. The positional shift amount derivation processing performed by the positional shift amount derivation unit 32 will be described later.

The reconstruction unit 33 generates a tomographic image emphasizing a desired tomographic plane of the breast M by reconstructing the projection image Gi while correcting the positional shift amount based on the body movement of the breast M derived by the positional shift amount derivation unit 32. Specifically, the reconstruction unit 33 generates a tomographic image on each of a plurality of tomographic planes of the breast M by reconstructing the projection image Gi while correcting the positional shift amount based on the body movement using, for example, a known back projection method such as a simple back projection method or a filtered back projection method. In this case, a three-dimensional coordinate position in a three-dimensional space including the breast M is set, pixel values of corresponding pixel positions of the plurality of projection images Gi are reconstructed for the set three-dimensional coordinate position, and the pixel value of the coordinate position is calculated. Here, in a case where the projection image Gi used for reconstruction is acquired in a state in which body movement occurs, the corresponding pixel position is corrected based on the positional shift amount. As a result, corresponding structures included in all the projection images Gi are reconstructed at the same three-dimensional coordinate position. In the present embodiment, it is assumed that the reconstruction unit 33 generates a temporary tomographic image first by reconstructing the projection image Gi without correcting the positional shift amount.

Hereinafter, positional shift amount derivation processing will be described. In the present embodiment, the reconstruction unit 33 generates a plurality of temporary tomographic images Dtj (j=1 to m, where m is the number of temporary tomographic images) by reconstructing the projection image Gi. Then, the positional shift amount derivation unit 32 detects feature points from the plurality of temporary tomographic images Dtj.

Figure 5:
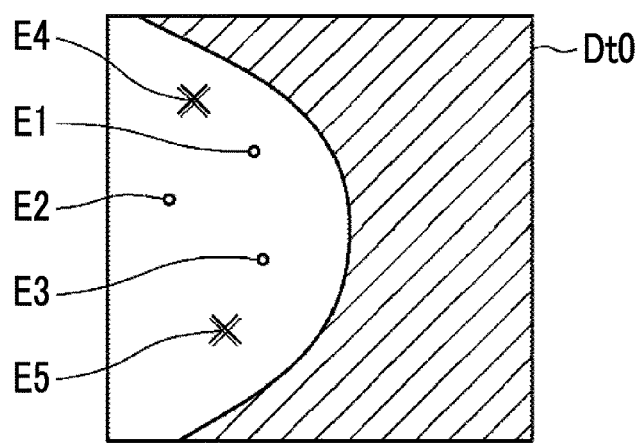
FIG. 5 is a diagram illustrating the detection of feature points from a temporary tomographic image.

FIG. 5 is a diagram illustrating the detection of feature points from a temporary tomographic image. Here, detection of feature points from one temporary tomographic image Dt0 will be described. As shown in FIG. 5, the temporary tomographic image Dt0 includes point-like structures E1 to E3, such as calcification, and intersections E4 and E5 of edges, such as intersections of blood vessels. The positional shift amount derivation unit 32 detects a point-like structure, such as calcification, as a feature point from the temporary tomographic image Dtj using an algorithm of known computer aided diagnosis (hereinafter, referred to as CAD). In addition, edges, intersections of edges, corners of edges, and the like included in the temporary tomographic image Dtj are detected as feature points using an algorithm, such as a Harris's corner detection method, a scale-invariant feature transform (SIFT), a features from accelerated segment test (FAST), or speeded up robust features (SURF). Then, the positional shift amount derivation unit 32 calculates the projection position of the feature point in the projection image Gi. The feature point may be only one pixel in the temporary tomographic image Dtj, or may be a plurality of pixels indicating the positions of feature structures.

Figure 6:
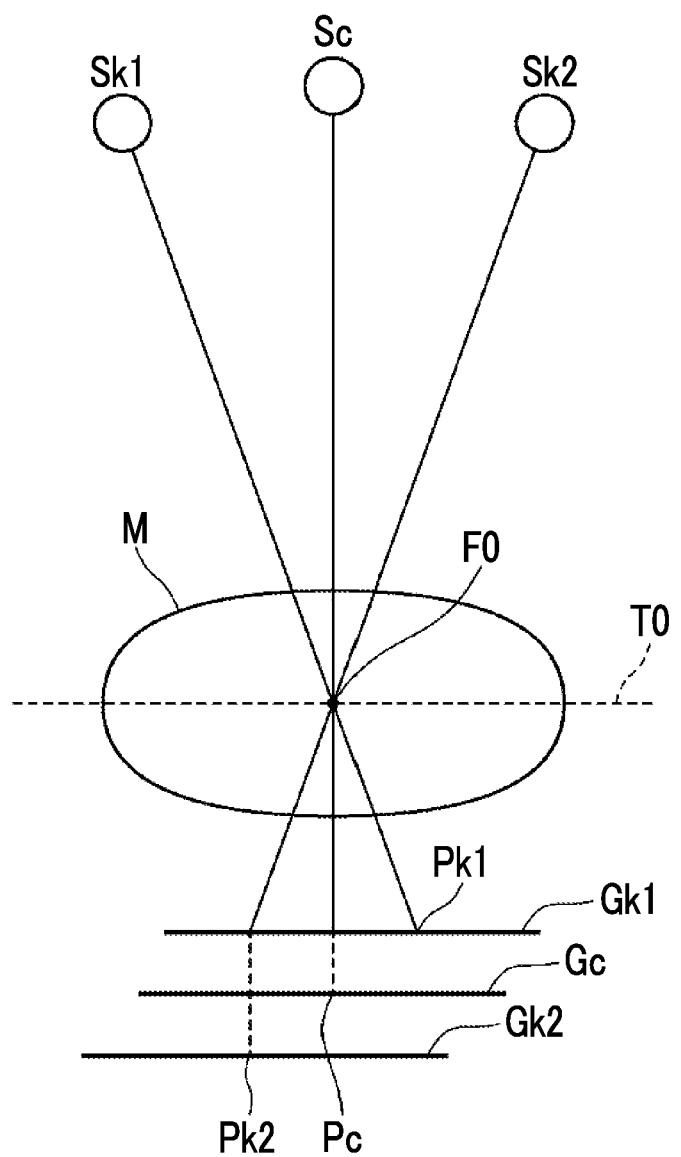
FIG. 6 is a diagram illustrating the calculation of a projection position of a feature point on a projection image.

FIG. 6 is a diagram illustrating the calculation of the projection position of a feature point on a projection image. In FIG. 6, in order to simplify the description, calculation of projection positions of a radiation source position Sk1, the reference radiation source position Sc, and a radiation source position Sk2 on corresponding three projection image Gk1, reference projection image Gc, and projection image Gk2 will be described. In FIG. 6, for the sake of description, three projection images are shown so as to be present on different planes. In practice, however, the three projection images are present on the same plane. In FIG. 6, it is assumed that one feature point F0 is detected in the temporary tomographic image Dt0 on a tomographic plane T0. Therefore, the feature point F0 is included in the tomographic plane T0. Here, for the sake of description, it is assumed that only one feature point F0 is projected. In practice, however, a plurality of different feature points are projected onto the projection image.

As shown in FIG. 6, at the time of imaging, the feature point F0 included in the tomographic plane T0 of the breast M is projected to positions Pk1, Pc, and Pk2 in the projection image Gk1, the reference projection image Gc, and the projection image Gk2. The radiation source position Sk1, the reference radiation source position Sc, the radiation source position Sk2, and the position of the feature point F0 in the breast M in the three-dimensional space are known. In addition, the position of the detection surface 15A of the radiation detector 15, on which the projection image Gk1, the reference projection image Gc, and the projection image Gk2 are generated, in the three-dimensional space is also known. Therefore, the positional shift amount derivation unit 32 calculates projection positions Pk1, Pc, and Pk2 of the feature point F0 at the radiation source position Sk1, the reference radiation source position Sc, and the radiation source position Sk2 based on the radiation source position Sk1, the reference radiation source position Sc, the radiation source position Sk2, and the position of the feature point F0 in the breast M in the three-dimensional space and the position of the detection surface of the radiation detector 15 where the projection image Gk1, the reference projection image Gc, and the projection image Gk2 are generated.

Figure 7:
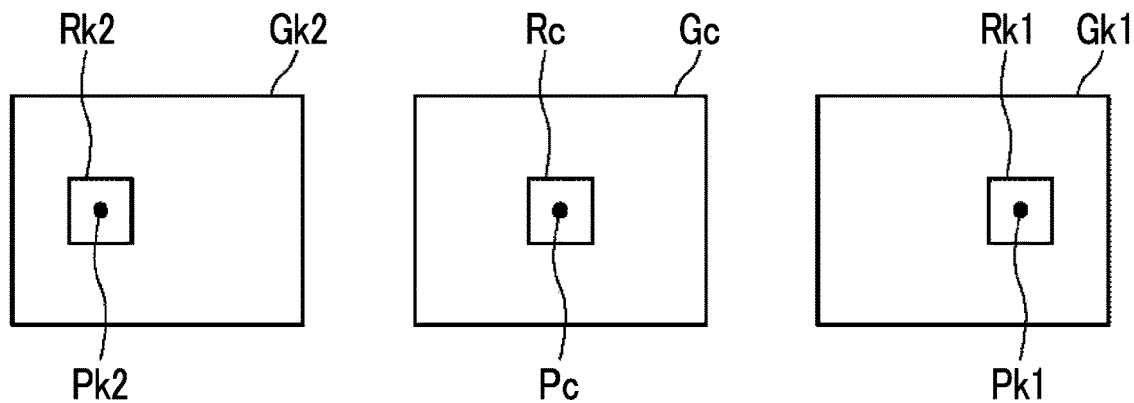
FIG. 7 is a diagram illustrating the setting of a region of interest.

Then, as shown in FIG. 7, the positional shift amount derivation unit 32 sets regions of interest Rk1, Rc, and Rk2, which have predetermined sizes centering on the projection positions Pk1, Pc, and Pk2, in the projection image Gk1, the reference projection image Gc, and the projection image Gk2. The positional shift amount derivation unit 32 performs registration of the regions of interest Rk1 and Rk2 with respect to the region of interest Rc using the reference projection image Gc as a reference, and derives, as a positional shift amount, a shift vector showing the movement direction and the movement amount of the regions of interest Rk1 and Rk2 with respect to the region of interest Rc. The registration means calculating the movement direction and the movement amount of the regions of interest Rk1 and Rk2 with respect to the region of interest Rc so that the correlation of the regions of interest Rk1 and Rk2 with respect to the region of interest Rc is maximized. Here, normalized cross correlation may be used as the correlation. In addition, since one reference projection image Gc of the projection images Gi is used as a reference, the number of shift vectors is smaller by one than the number of projection images. For example, in a case where the number of projection images is 15, the number of shift vectors is 14. In a case where the number of projection images is 3, the number of shift vectors is 2.

Figure 8:
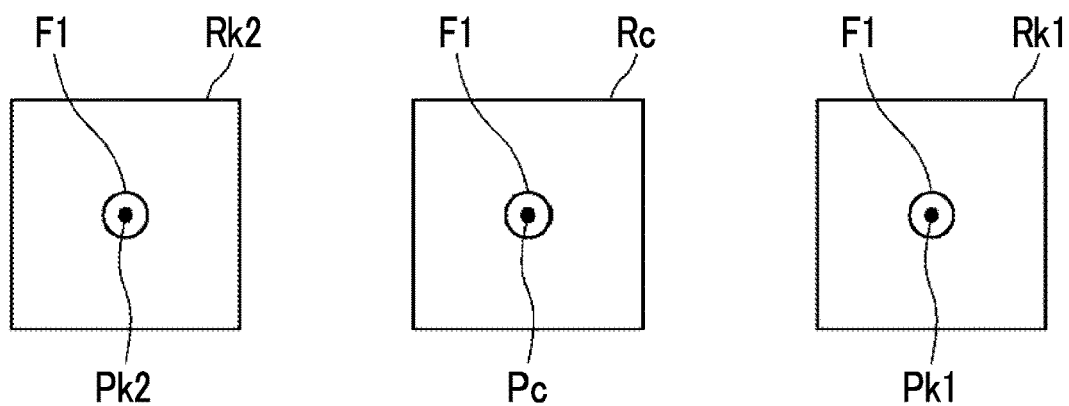
FIG. 8 is a diagram showing images in three regions of interest in a case where no body movement occurs.

FIG. 8 is a diagram showing images in the three regions of interest Rk1, Rc, and Rk2 in a case where no body movement occurs while acquiring the projection image Gk1, the reference projection image Gc, and the projection image Gk2. In FIG. 8, an image F1 of the feature point F0 included in the regions of interest Rk1, Rc, and Rk2 is shown by a circle larger than the projection positions Pk1, Pc, and Pk2. As shown in FIG. 8, in a case where no body movement occurs while acquiring the projection image Gk1, the reference projection image Gc, and the projection image Gk2, the projection positions Pk1, Pc, and Pk2 and the position of the image F1 of the feature point included in the regions of interest Rk1, Rc, and Rk2 match each other in all of the three regions of interest Rk1, Rc, and Rk2. For this reason, shift vectors, that is, positional shift amounts of the regions of interest Rk1 and Rk2 with respect to the region of interest Rc are all 0.

Figure 9:
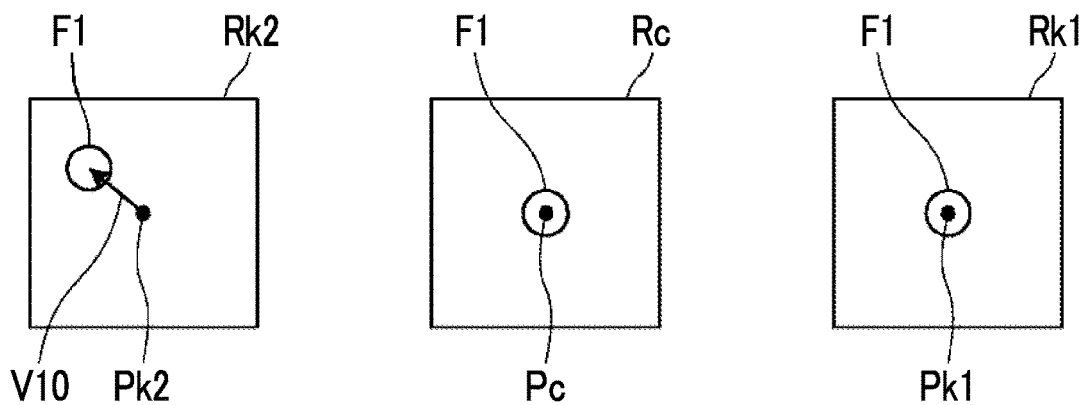
FIG. 9 is a diagram showing images in three regions of interest in a case where body movement occurs.

FIG. 9 is a diagram showing images in the three regions of interest Rk1, Rc, and Rk2 in a case where body movement occurs while acquiring the reference projection image Gc and the projection image Gk2 among the projection image Gk1, the reference projection image Gc, and the projection image Gk2. In FIG. 9, since no body movement occurs while acquiring the projection image Gk1 and the reference projection image Gc, the projection positions Pk1 and Pc in the regions of interest Rk1 and Rc and the position of the image F1 of the feature point included in the regions of interest Rk1 and Rc match each other. For this reason, the positional shift amount of the region of interest Rk1 with respect to the region of interest Rc is 0. On the other hand, since body movement occurs while acquiring the reference projection image Gc and the projection image Gk2, the projection position Pk2 in the region of interest Rk2 and the position of the image F1 of the feature point included in the region of interest Rk2 do not match each other. Therefore, due to the movement amount and the movement direction of the region of interest Rk2 with respect to the region of interest Rc, a shift vector V10 having a size and a direction is derived. The derived shift vector V10 is the positional shift amount.

Figure 10:
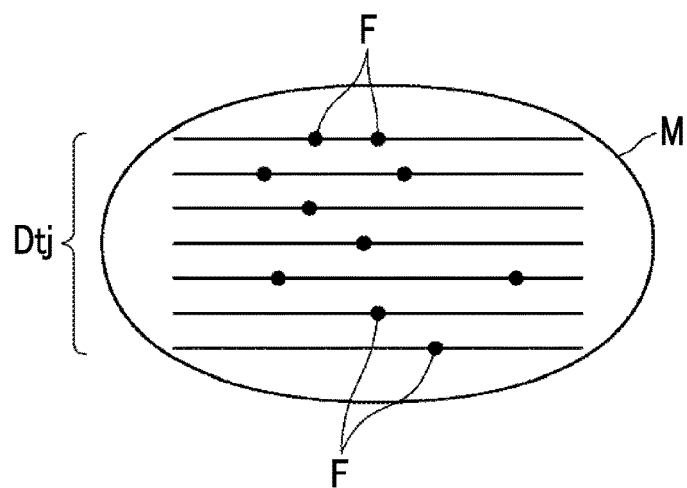
FIG. 10 is a diagram showing feature points in a three-dimensional space.

In the above, one feature point F0 is detected in one temporary tomographic image Dtj, and the positional shift amounts of a plurality of projection images with respect to the reference projection image Gc are derived for only one feature point F0. In practice, however, as shown in FIG. 10, the positional shift amount derivation unit 32 derives a positional shift amount for a plurality of different feature points F (here, ten feature points shown by black circles) in a three-dimensional space in the breast M expressed by the plurality of temporary tomographic images Dtj. As a result, for the projection image acquired in a state in which body movement occurs, positional shift amounts for a plurality of different feature points F are derived. The positional shift amount derivation unit 32 interpolates the positional shift amounts for the plurality of different feature points F with respect to all coordinate positions of the three-dimensional space for generating a tomographic image. As a result, for the projection image acquired in a state in which body movement occurs, the positional shift amount derivation unit 32 derives a positional shift amount at the time of performing reconstruction for all the coordinate positions of the three-dimensional space for generating a tomographic image.

Figure 11:
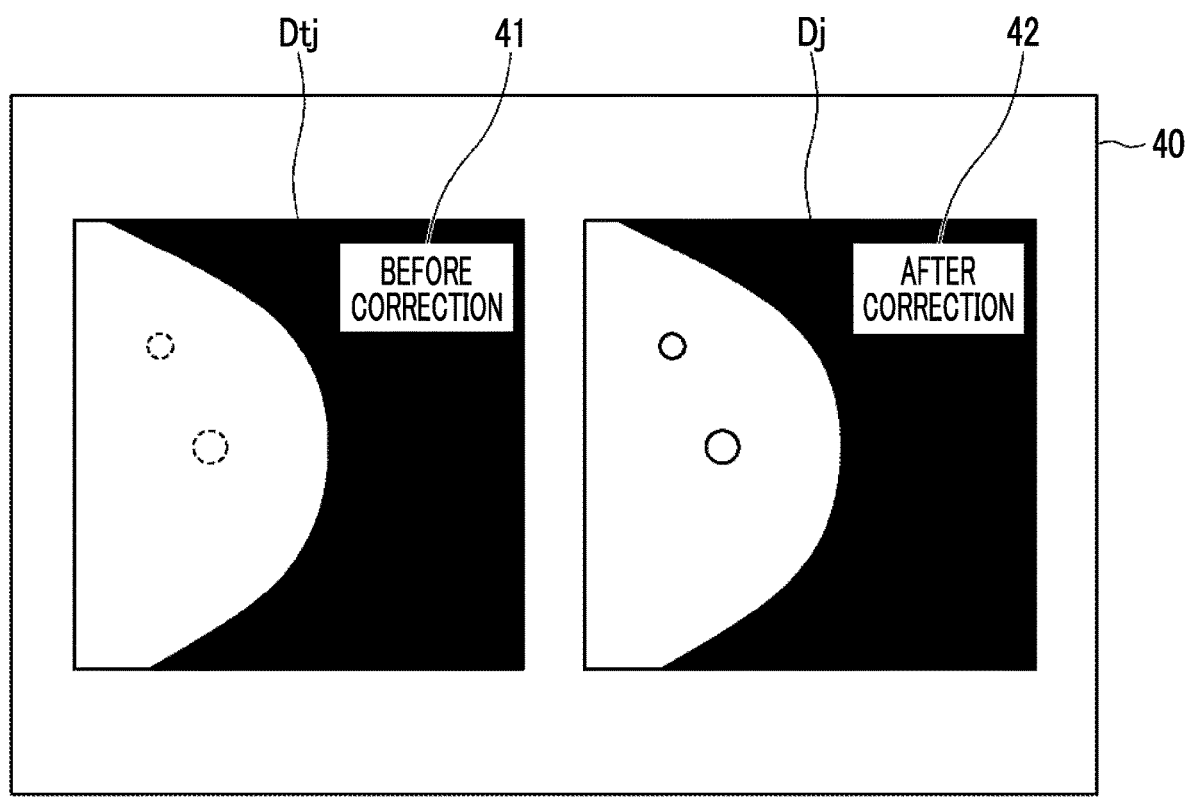
FIG. 11 is a diagram showing a display screen of a tomographic image.

The display controller 34 displays the generated tomographic image on the display unit 3. FIG. 11 is a diagram showing a display screen of a tomographic image. As shown in FIG. 11, the temporary tomographic image Dtj before body movement correction and a tomographic image Dj after body movement correction are displayed on a display screen 40. A label 41 of "before correction" is given to the temporary tomographic image Dtj so that it can be seen that body movement correction has not been made. A label 42 of "after correction" is given to the tomographic image Dj so that it can be seen that body movement correction has been made. The label 41 may be given only to the temporary tomographic image Dtj, and the label 42 may be given only to the tomographic image Dj. It is needless to say that only the tomographic image Dj subjected to body movement correction may be displayed.

It is preferable that the temporary tomographic image Dtj and the tomographic image Dj show the same tomographic plane. In the case of switching the tomographic plane to be displayed in response to an instruction from the input unit 4, it is preferable to link the tomographic planes to be displayed in the temporary tomographic image Dtj and the tomographic image Dj. In addition to the temporary tomographic image Dtj and the tomographic image Dj, the projection image Gi may be displayed.

The operator can check the success or failure of the body movement correction while viewing the display screen 40. In a case where the body movement is too large, even though a tomographic image is generated by performing reconstruction while correcting the positional shift amount as in the present embodiment, the body movement cannot be corrected accurately. Accordingly, the body movement correction may fail. In such a case, the temporary tomographic image Dtj may have a higher image quality than the tomographic image Dj. For this reason, an instruction regarding which of the temporary tomographic image Dtj and the tomographic image Dj is to be stored may be received through the input unit 4, and the designated image may be stored in the storage 23 or the external storage device.

Figure 12:
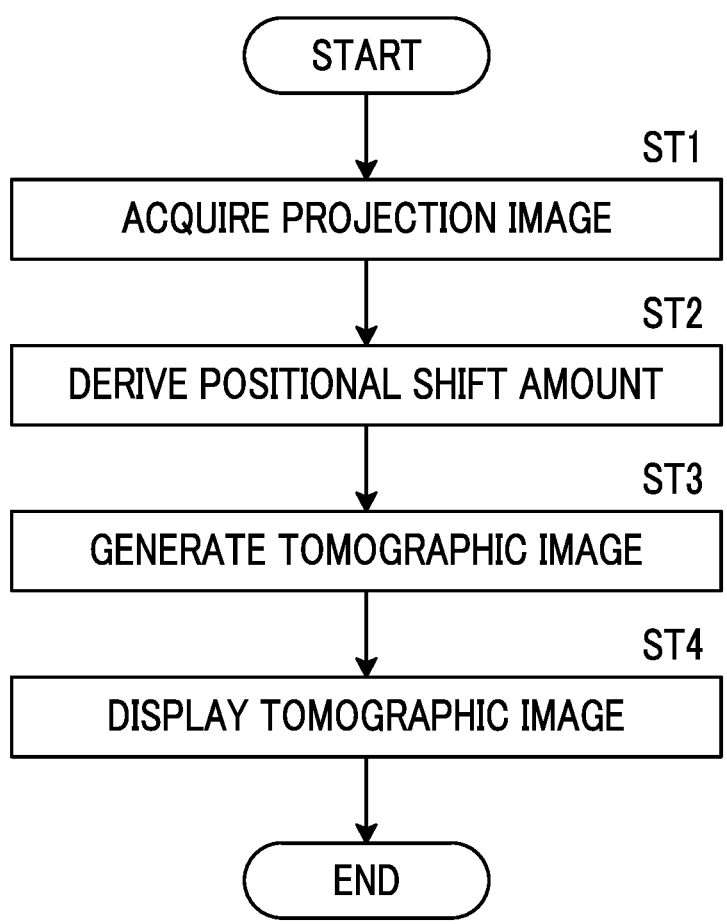
FIG. 12 is a flowchart showing the process performed in the first embodiment.

Next, the process performed in the first embodiment will be described. FIG. 12 is a flowchart showing the process performed in the first embodiment. In a case where an operator's instruction to start the process is received through the input unit 4, the image acquisition unit 31 causes the radiation image capturing apparatus 1 to perform tomosynthesis imaging to acquire a plurality of projection images Gi (step ST1). Then, the positional shift amount derivation unit 32 derives a positional shift amount between the plurality of projection images Gi with the reference projection image Gc as a reference (step ST2). Then, the reconstruction unit 33 generates a tomographic image by reconstructing the plurality of projection images Gi while correcting the positional shift amount (step ST3). Then, the display controller 34 displays the tomographic image on the display unit 3 (step ST4), and the process is ended.

Thus, according to the first embodiment, a plurality of projection images Gi are acquired by tomosynthesis imaging, and the positional shift amount between a plurality of projection images is derived with the reference projection image Gc generated at the radiation source position Sc where the optical axis X0 of the X-ray emitted from the X-ray source 16 is perpendicular to the detection surface 15A of the radiation detector 15, among the plurality of projection images Gi, as a reference. Then, the plurality of projection images Gi are reconstructed while correcting the positional shift amount to generate the tomographic image Dj on at least one tomographic plane of the breast M.

In the first embodiment, by using such a reference projection image Gc as a reference, it is possible to derive the positional shift amount between a plurality of projection images so as to match a simply captured image. Therefore, by reconstructing the projection images while correcting the derived positional shift amount, it is possible to acquire a high-quality tomographic image in which the influence of body movement is appropriately reduced. In addition, the correspondence between the position of the tomographic image subjected to body movement correction and the position of the two-dimensional image acquired by simple imaging can be easily taken.

Figure 13:
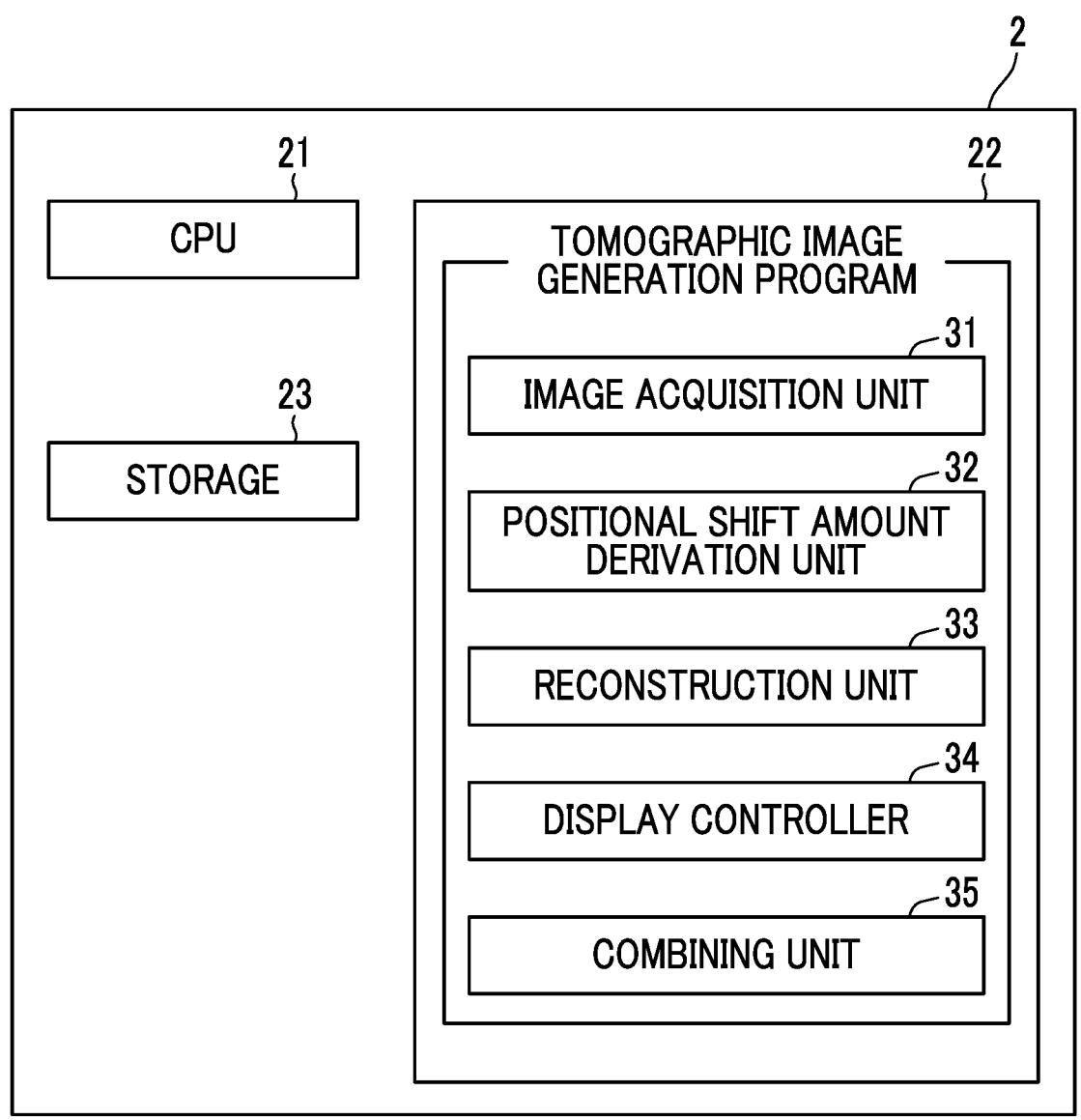
FIG. 13 is a diagram showing the schematic configuration of an imaging control device realized by installing a tomographic image generation program on a computer in a second embodiment.

Next, a second embodiment of the invention will be described. FIG. 13 is a diagram showing the schematic configuration of a tomographic image generation apparatus realized by installing a tomographic image generation program according to the second embodiment on the computer 2. In FIG. 13, the same components as in FIG. 3 are denoted by the same reference numerals as in FIG. 3, and the detailed description thereof will be omitted herein. The tomographic image generation apparatus according to the second embodiment is different from the tomographic image generation apparatus according to the first embodiment in that the tomographic image generation apparatus according to the second embodiment further comprises a combining unit 35 that generates a composite two-dimensional image by combining two or more tomographic images among a plurality of tomographic images or at least one of the plurality of tomographic images and the reference projection image Gc.

In the second embodiment, the combining unit 35 generates a composite two-dimensional image using, for example, the method described in JP2014-128716A. The method described in JP2014-128716A is a method of generating a composite two-dimensional image by projecting two or more tomographic images among a plurality of tomographic images or at least one of the plurality of tomographic images and the reference projection image Gc in the depth direction of the subject in which the tomographic planes are aligned. The method of generating a composite two-dimensional image is not limited to this. For example, by adding up the pixel values of the pixel positions corresponding to each other in the depth direction of the breast M, in which the tomographic planes are aligned, for two or more tomographic images among a plurality of tomographic images or at least one of the plurality of tomographic images and the reference projection image Gc, a composite two-dimensional image may be generated. Alternatively, by projecting two or more tomographic images among a plurality of tomographic images or at least one of the plurality of tomographic images and the reference projection image Gc in the depth direction of the breast M, in which the tomographic planes are aligned, using a minimum value projection method, a composite two-dimensional image may be generated.

In the second embodiment, since a composite two-dimensional image is generated using the tomographic image subjected to body movement correction as in the first embodiment, the correspondence between the position of the generated composite two-dimensional image and the position of the two-dimensional image acquired by simple imaging can be easily taken.

In the second embodiment, the display controller 34 may display the composite two-dimensional image on the display unit 3 together with the tomographic image.

In addition, although the positional shift amount derivation unit 32 derives the positional shift amount using the temporary tomographic image Dtj in each of the embodiments described above, the invention is not limited thereto. For example, at least one, preferably, a plurality of corresponding points may be detected between a plurality of projection images Gi, the corresponding points in the plurality of projection images Gi may be projected onto a desired tomographic plane of the breast M based on the positional relationship between the radiation detector 15 and the radiation source position at the time of imaging for each of the plurality of projection images Gi, and the positional shift amount may be derived based on the positional relationship between the projected corresponding points. Hereinafter, this will be described as a third embodiment.

Figure 14:
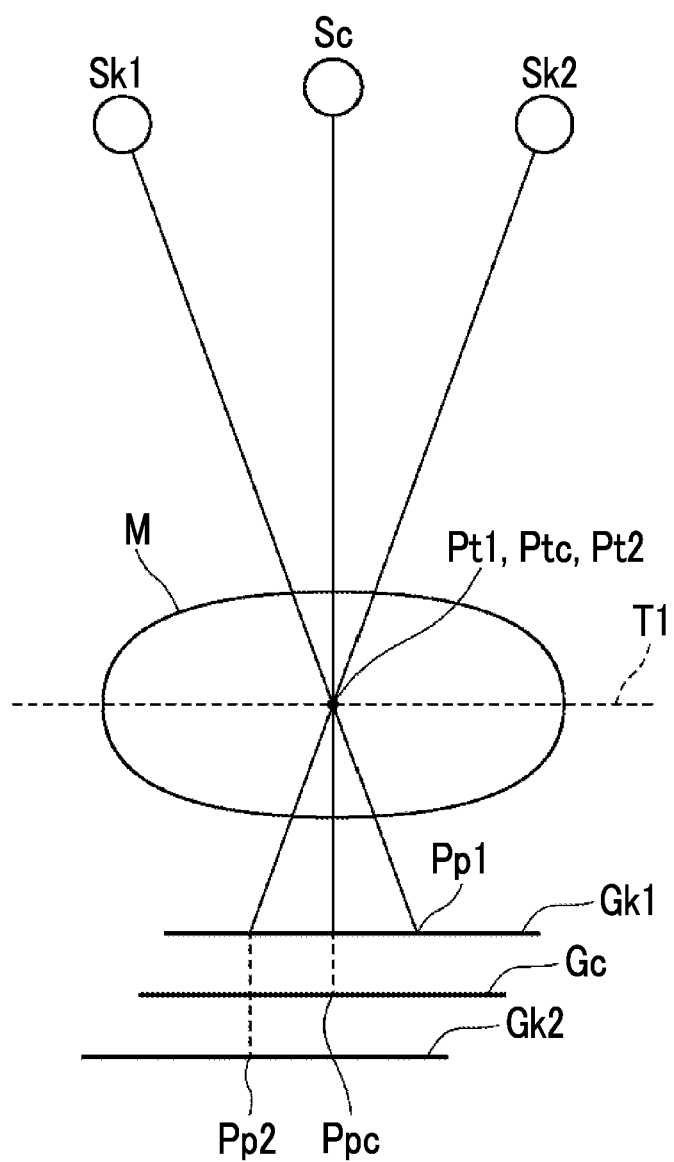
FIG. 14 is a diagram illustrating the projection of a projection image onto a tomographic plane for derivation of a positional shift amount in a third embodiment.

FIG. 14 is a diagram illustrating the projection of a projection image on a tomographic plane for derivation of the positional shift amount in the third embodiment. In FIG. 14, in order to simplify the description, projection of corresponding points, which are detected in three projection image Gk1, reference projection image Gc, and projection image Gk2 corresponding to the radiation source position Sk1, the reference radiation source position Sc, and the radiation source position Sk2, onto a tomographic plane T1 in the breast M will be described. First, the positional shift amount derivation unit 32 detects corresponding points Pp1, Ppc, and Pp2 corresponding to one another in the three projection image Gk1, reference projection image Gc, and projection image Gk2. The detection of the corresponding points Pp1, Ppc, and Pp2 may be performed in the same manner as the detection of feature points from the temporary tomographic image Dtj in the first embodiment.

Here, in a case where no body movement occurs while acquiring the projection image Gk1, the reference projection image Gc, and the projection image Gk2, projection positions Pt1, Ptc, and Pt2 of the corresponding points Pp1, Ppc, and Pp2, which are included in the three projection image Gk1, reference projection image Gc, and projection image Gk2, on the tomographic plane T1 are the same. For this reason, the positional shift amount between the projection image Gk1, the reference projection image Gc, and the projection image Gk2 is 0.

Figure 15:
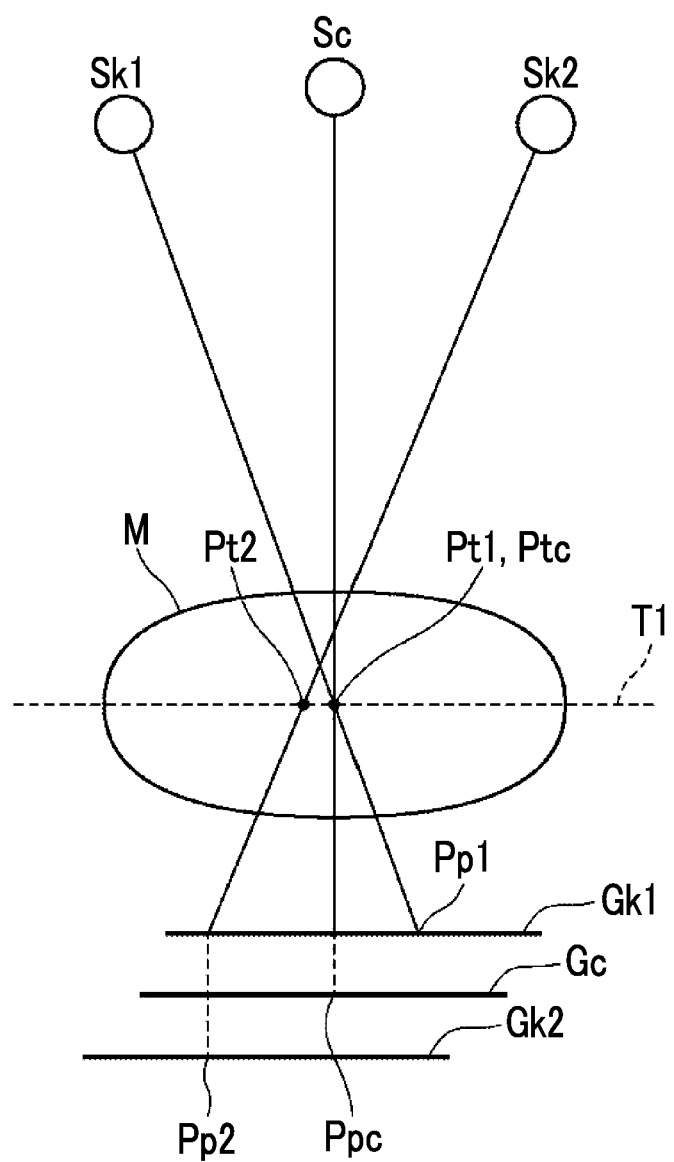
FIG. 15 is a diagram illustrating the projection of a projection image onto a tomographic plane for derivation of a positional shift amount in a case where body movement occurs in the third embodiment.

FIG. 15 is a diagram showing the projection of a projection image onto a tomographic plane for derivation of the positional shift amount in a case where body movement occurs while acquiring the reference projection image Gc and the projection image Gk2 among the projection image Gk1, the reference projection image Gc, and the projection image Gk2 in the third embodiment. In FIG. 15, since no body movement occurs while acquiring the projection image Gk1 and the reference projection image Gc, the projection positions Pt1 and Ptc of the corresponding points Pp1 and Ppc on the tomographic plane T1 are the same. For this reason, the positional shift amount of the projection image Gk1 with respect to the reference projection image Gc is 0.

On the other hand, since body movement occurs while acquiring the reference projection image Gc and the projection image Gk2, the projection position Pt2 of the corresponding point Pp2 on the tomographic plane T1 does not match the projection position Ptc of the corresponding point Ppc on the tomographic plane T1 in the reference projection image Gc.

Figure 16:
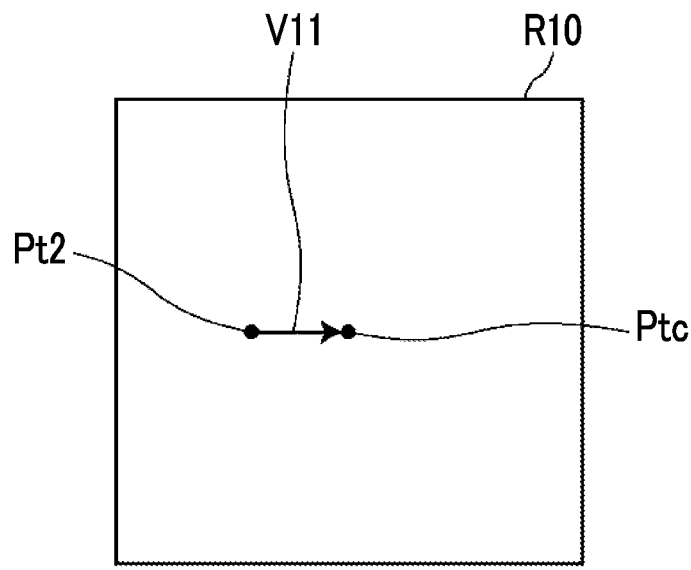
FIG. 16 is a diagram showing a region of interest including the projection position of a corresponding point of a reference projection image.

The positional shift amount derivation unit 32 extracts a region of interest including the projection position of the corresponding point Ppc of the reference projection image Gc from the image projected onto the tomographic plane T1. FIG. 16 is a diagram showing a region of interest including the projection position Ptc of the corresponding point Ppc of the reference projection image Gc. As shown in FIG. 16, a region of interest R10 includes the projection position Ptc of the corresponding point Ppc of the reference projection image Gc and the projection position Pt2 of the corresponding point Pp2 of the projection image Gk2. In the region of interest R10, the positional shift amount derivation unit 32 derives a movement amount and a movement direction for making the projection position Pt2 match the projection position Ptc as a shift vector V11, that is, a positional shift amount.

In the third embodiment, one corresponding point is detected in the plurality of projection images Gi, the one corresponding point is projected onto one tomographic plane T1, and the positional shift amounts of the plurality of projection images with respect to the reference projection image Gc are derived. In practice, however, the positional shift amount derivation unit 32 detects a plurality of corresponding points between the projection images Gi, and projects the plurality of projection images Gi onto a plurality of tomographic planes for generating a plurality of tomographic images. Then, on the tomographic images of the plurality of tomographic planes, the positional shift amounts of the corresponding points in the plurality of projection images Gi with respect to the reference projection image Gc are derived. Then, by interpolating the positional shift amounts for the plurality of corresponding points with respect to the coordinate position of each tomographic plane, a positional shift amount at the time of performing reconstruction is derived for all coordinate positions in the three-dimensional space for generating a tomographic image in a projection image acquired in a state in which body movement occurs.

Also by deriving the positional shift amount as in the third embodiment, a high-quality tomographic image in which the influence of body movement is reduced can be acquired by the reconstruction unit 33 that reconstructs a plurality of projection images while correcting the positional shift amount.

Figure 17:
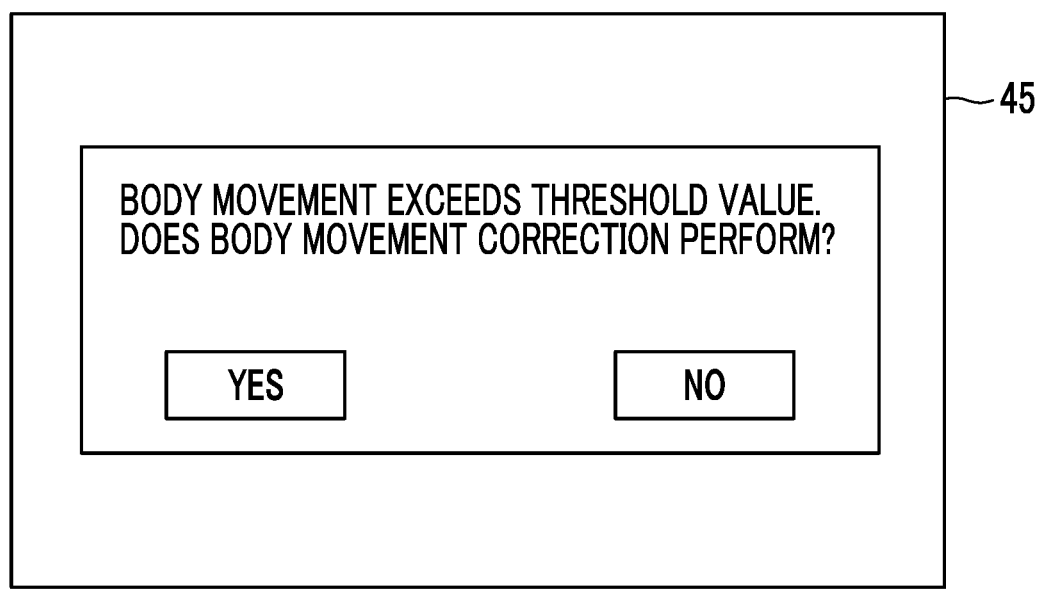
FIG. 17 is a diagram showing a warning display.

In each of the embodiments described above, the positional shift amount derived by the positional shift amount derivation unit 32 may be compared with a predetermined threshold value, and the tomographic image may be reconstructed while correcting the positional shift amount only in a case where the positional shift amount exceeds the threshold value. In this case, as shown in FIG. 17, a warning display 45 for notifying that the body movement exceeds the threshold value may be displayed on the display unit 3. The threshold value may be set to a value at which it can be said that there is no influence of body movement on the tomographic image without correcting the positional shift amount. The operator can give an instruction as to whether or not to perform body movement correction by selecting a command of YES or NO on the warning display 45.

In the first embodiment described above, in order to easily derive a shift vector, a region of interest is set at the projection position of the feature point, and the movement direction and the movement amount of the region of interest are derived as a shift vector, that is, a positional shift amount. However, the invention is not limited thereto. The movement direction and the movement amount between the projection images of the projection positions of the feature points may be derived as the positional shift amount without setting the region of interest.

In the third embodiment described above, in order to easily derive a shift vector, a region of interest is set at the projection position of the corresponding point on the tomographic plane, and the movement direction and the movement amount of the region of interest are derived as a shift vector, that is, a positional shift amount. However, the invention is not limited thereto. The movement direction and the movement amount of the projection position of the corresponding point with respect to the projection position of the corresponding point of the reference projection image Gc may be derived as the positional shift amount without setting the region of interest.

In each of the embodiments described above, the subject is the breast M. However, the invention is not limited thereto, and it is needless to say that any part, such as the chest or abdomen of a human body, may be the subject.

In the embodiment described above, for example, various processors shown below can be used as the hardware structures of processing units for executing various kinds of processing, such as the image acquisition unit 31, the positional shift amount derivation unit 32, the reconstruction unit 33, the display controller 34, and the combining unit 35. The various processors include not only the above-described CPU, which is a general-purpose processor that executes software (program) to function as various processing units, but also a programmable logic device (PLD) that is a processor whose circuit configuration can be changed after manufacture, such as a field programmable gate array (FPGA), and a dedicated electric circuit that is a processor having a circuit configuration that is designed for exclusive use in order to execute specific processing, such as an application specific integrated circuit (ASIC).

One processing unit may be configured by one of various processors, or may be a combination of two or more processors of the same type or different types (for example, a combination of a plurality of FPGAs or a combination of a CPU and an FPGA). Alternatively, a plurality of processing units may be configured by one processor.

As an example of configuring a plurality of processing units using one processor, first, as represented by a computer, such as a client and a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as a hardware structure.

More specifically, as the hardware structure of these various processors, it is possible to use an electrical circuit (circuitry) in which circuit elements, such as semiconductor elements, are combined.

In addition to the program, the invention also extends to a non-transitory recording medium in which the program is recorded.

What is claimed is:

1. A tomographic image generation apparatus, comprising:
    an image acquisition unit, which is a processor, that acquires a plurality of projection images corresponding to a plurality of radiation source positions, the plurality of projection images being generated by causing an imaging apparatus to perform tomosynthesis imaging in which a radiation source is moved relative to a radiation detector in order to emit radiation to a subject at the plurality of radiation source positions according to movement of the radiation source;
    a positional shift amount derivation unit, which is a processor, that derives a positional shift amount between the plurality of projection images based on body movement of the subject with a reference projection image generated at a radiation source position where an optical axis of the radiation emitted from the radiation source is perpendicular to a detection surface of the radiation detector, among the plurality of projection images, as a reference;
    a reconstruction unit, which is a processor, that generates a tomographic image of at least one tomographic plane of the subject by reconstructing the plurality of projection images while correcting the positional shift amount;
    wherein the reconstruction unit reconstructs the plurality of projection images to generate a plurality of temporary tomographic images, and
    the positional shift amount derivation unit detects a plurality of different feature points in the plurality of temporary tomographic images, derives a temporary positional shift amount between the plurality of projection images with the reference projection image as a reference for the plurality of different feature points, interpolates temporary positional shift amounts derived for the plurality of different feature points, and derives a positional shift amount of each pixel position in each of the plurality of projection images with respect to each of coordinate positions of the plurality of temporary tomographic images.

2. The tomographic image generation apparatus according to claim 1 wherein:
    the reconstruction unit generates a plurality of tomographic images; and
    the tomographic image generation apparatus further comprises a combining unit, which is a processor, that generates a composite two-dimensional image by combining two or more tomographic images among the plurality of tomographic images or at least one of the plurality of tomographic images and the reference projection image.

3. The tomographic image generation apparatus according to claim 1,
    wherein the subject is a breast.

4. A tomographic image generation apparatus, comprising:
    an image acquisition unit, which is a processor, that acquires a plurality of projection images corresponding to a plurality of radiation source positions, the plurality of projection images being generated by causing an imaging apparatus to perform tomosynthesis imaging in which a radiation source is moved relative to a radiation detector in order to emit radiation to a subject at the plurality of radiation source positions according to movement of the radiation source;

a positional shift amount derivation unit, which is a processor, that derives a positional shift amount between the plurality of projection images based on body movement of the subject with a reference projection image generated at a radiation source position where an optical axis of the radiation emitted from the radiation source is perpendicular to a detection surface of the radiation detector, among the plurality of projection images, as a reference; and a reconstruction unit, which is a processor, that generates a tomographic image of at least one tomographic plane of the subject by reconstructing the plurality of projection images while correcting the positional shift amount;

wherein the positional shift amount derivation unit detects at least one corresponding point in the plurality of projection images, projects the corresponding points in the plurality of projection images onto at least one tomographic plane of the subject based on a positional relationship between the radiation detector and the radiation source position at the time of imaging for each of the plurality of projection images, and derives the positional shift amount based on a positional relationship between the projected corresponding points.

5. The tomographic image generation apparatus according to claim 4 wherein:

the reconstruction unit generates a plurality of tomographic images; and the tomographic image generation apparatus further comprises a combining unit, which is a processor, that generates a composite two-dimensional image by combining two or more tomographic images among the plurality of tomographic images or at least one of the plurality of tomographic images and the reference projection image.

6. The tomographic image generation apparatus according to claim 4, wherein the subject is a breast.

7. A tomographic image generation method, comprising:

acquiring a plurality of projection images corresponding to a plurality of radiation source positions, the plurality of projection images being generated by causing an imaging apparatus to perform tomosynthesis imaging in which a radiation source is moved relative to a radiation detector in order to emit radiation to a subject at the plurality of radiation source positions according to movement of the radiation source;

generating a plurality of temporary tomographic images;

deriving a positional shift amount between the plurality of projection images based on body movement of the subject with a reference projection image generated at a radiation source position where an optical axis of the radiation emitted from the radiation source is perpendicular to a detection surface of the radiation detector, among the plurality of projection images, as a reference by detecting a plurality of different feature points in the plurality of temporary tomographic images, deriving a temporary positional shift amount between the plurality of projection images with the reference projection image as a reference for the plurality of different feature points, interpolates temporary positional shift amounts derived for the plurality of different feature points, and deriving a positional shift amount of each pixel position in each of the plurality of projection images with respect to each of coordinate positions of the plurality of temporary tomographic images; and generating a tomographic image of at least one tomographic plane of the subject by reconstructing the plurality of projection images while correcting the positional shift amount among the plurality of projection images.

8. A non-transitory computer-readable storage medium that stores a tomographic image generation program causing a computer to execute:

a step of acquiring a plurality of projection images corresponding to a plurality of radiation source positions, the plurality of projection images being generated by causing an imaging apparatus to perform tomosynthesis imaging in which a radiation source is moved relative to a radiation detector in order to emit radiation to a subject at the plurality of radiation source positions according to movement of the radiation source;

a step of generating a plurality of temporary tomographic images;

a step of deriving a positional shift amount between the plurality of projection images based on body movement of the subject with a reference projection image generated at a radiation source position where an optical axis of the radiation emitted from the radiation source is perpendicular to a detection surface of the radiation detector, among the plurality of projection images, as a reference by detecting a plurality of different feature points in the plurality of temporary tomographic images, deriving a temporary positional shift amount between the plurality of projection images with the reference projection image as a reference for the plurality of different feature points, interpolates temporary positional shift amounts derived for the plurality of different feature points, and deriving a positional shift amount of each pixel position in each of the plurality of projection images with respect to each of coordinate positions of the plurality of temporary tomographic images; and a step of generating a tomographic image of at least one tomographic plane of the subject by reconstructing the plurality of projection images while correcting the positional shift amount among the plurality of projection images.

9. A tomographic image generation method, comprising:

acquiring a plurality of projection images corresponding to a plurality of radiation source positions, the plurality of projection images being generated by causing an imaging apparatus to perform tomosynthesis imaging in which a radiation source is moved relative to a radiation detector in order to emit radiation to a subject at the plurality of radiation source positions according to movement of the radiation source;

detecting at least one corresponding point in the plurality of projection images, projecting the corresponding points in the plurality of projection images onto at least one tomographic plane of the subject based on a positional relationship between the radiation detector and the radiation source position at the time of imaging for each of the plurality of projection images, and, based on a positional relationship between the projected corresponding points, deriving a positional shift amount between the plurality of projection images based on body movement of the subject with a reference projection image generated at a radiation source position where an optical axis of the radiation emitted from the radiation source is perpendicular to a detection surface of the radiation detector, among the plurality of projection images, as a reference; and generating a tomographic image of at least one tomographic plane of the subject by reconstructing the plurality of projection images while correcting the positional shift amount.

10. A non-transitory computer-readable storage medium that stores a tomographic image generation program causing a computer to execute:

a step of acquiring a plurality of projection images corresponding to a plurality of radiation source positions, the plurality of projection images being generated by causing an imaging apparatus to perform tomosynthesis imaging in which a radiation source is moved relative to a radiation detector in order to emit radiation to a subject at the plurality of radiation source positions according to movement of the radiation source;

a step of detecting at least one corresponding point in the plurality of projection images, projecting the corresponding points in the plurality of projection images onto at least one tomographic plane of the subject based on a positional relationship between the radiation detector and the radiation source position at the time of imaging for each of the plurality of projection images, and, based on a positional relationship between the projected corresponding points, deriving a positional shift amount between the plurality of projection images based on body movement of the subject with a reference projection image generated at a radiation source position where an optical axis of the radiation emitted from the radiation source is perpendicular to a detection surface of the radiation detector, among the plurality of projection images, as a reference; and a step of generating a tomographic image of at least one tomographic plane of the subject by reconstructing the plurality of projection images while correcting the positional shift amount.

\* \* \* \* \*